United States Patent [19]

Portmann

[11] 4,401,600
[45] Aug. 30, 1983

[54] CERTAIN 3-PHENYLHYDRAZONO-2-AMINO-1,1,3-PROPENE TRICARBONITRILE

[75] Inventor: Robert Portmann, Pratteln, Switzerland

[73] Assignee: Ciba-Geigy Corporation, Ardsley, N.Y.

[21] Appl. No.: 294,253

[22] Filed: Aug. 18, 1981

Related U.S. Application Data

[62] Division of Ser. No. 122,785, Feb. 19, 1980, abandoned, which is a division of Ser. No. 42,696, May 25, 1979, Pat. No. 4,243,583.

[30] Foreign Application Priority Data

Jun. 2, 1978 [CH] Switzerland ............ 6077/78

[51] Int. Cl.³ ............................ C07D 109/16
[52] U.S. Cl. .................................. 260/465 E
[58] Field of Search ................... 260/465 E

[56] References Cited

U.S. PATENT DOCUMENTS 4,309,181  1/1982  Rau ........................ 260/465 E

FOREIGN PATENT DOCUMENTS 1101727  4/1968  United Kingdom .
1326124  1/1973  United Kingdom .

Primary Examiner—Henry R. Jiles
Assistant Examiner—Bernard Dentz
Attorney, Agent, or Firm—Edward McC. Roberts

[57] ABSTRACT

The invention relates to a process for the preparation of azo dyes of the formula

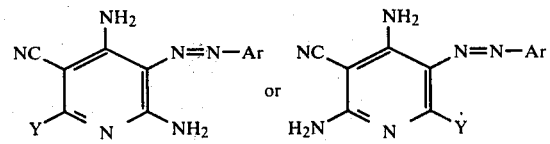

or mixtures thereof, in which Ar is a substituted or unsubstituted phenyl, naphthyl or aromatic heterocyclic radical and Y is a group of the formula —O—R, —S—R or

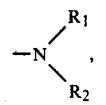

in which R is a substituted or unsubstituted alkyl, aryl or heterocyclic radical and $R_1$ and $R_2$ independently of one another are hydrogen or a substituted or unsubstituted alkyl, aryl or heterocyclic radical, and the groups $R_1$ and $R_2$, together with the nitrogen atom to which they are bonded, can form a ring.

The process comprises first coupling dimeric malonodinitrile with a diazo component and cyclizing the resulting intermediate with an alcohol, thioalcohol or amine.

3 Claims, No Drawings

CERTAIN 3-PHENYLHYDRAZONO-2-AMINO-1,1,3-PROPENE TRICARBONITRILE

This is a division of application Ser. No. 122,785 filed on Feb. 19, 1980 now abandoned, which in turn is a division of Ser. No. 042,696 filed May 25, 1979, now U.S. Pat. No. 4,243,583.

The present invention relates to a process for the preparation of azo dyes, these dyes, if they are novel, compounds which are obtained as intermediates from the preparation of the dyes, a process for the preparation of these compounds and a process for dyeing or printing hydrophobic synthetic fibres.

German Offenlegungsschrift No. 2,263,007 discloses azo dyes of the formula

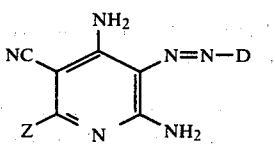

in which D is a diazo component and Z is the radical of an alcohol, thioalcohol or amine. These dyes are prepared by coupling a diazotised amine with the corresponding substituted pyridine derivatives, which are accessible by reacting malonodinitrile with HBr and subsequently replacing the Br by the radical of an alcohol, thioalcohol or amine.

However, with this reaction it is necessary to work under anhydrous conditions and to use HBr, which is very expensive.

The object on which the present invention was based was, therefore, to find a more advantageous process for the preparation of such dyes.

It has now been found that such dyes can be obtained in a considerably simpler manner by first coupling dimeric malonodinitrile (2-amino-1,1,3-tricyano-1-propene) with a diazo compound and then cyclising the resulting intermediate in the presence of an alcohol, thioalcohol or amine.

Surprisingly, the cyclisation can be carried out without HBr and also in an aqueous medium and dyes of the above formula and/or isomers of these compounds are obtained in good yields, the mixtures frequently being distinguished by the fact that they give a better colour yield than the individual dyes on dyeing. A considerable advantage of the process according to the invention is the possibility for carrying out the cyclisation in water. This was not possible hitherto.

The invention relates to a process for the preparation of azo dyes of the formula

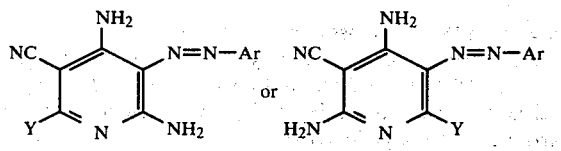

or their mixtures, in which Ar is a substituted or unsubstituted phenyl, naphthyl or aromatic heterocyclic radical and Y is a group of the formula —O—R, —S—R or

in which R is a substituted or unsubstituted alkyl, aryl or heterocyclic radical and $R_1$ and $R_2$ independently of one another are hydrogen or a substituted or unsubstituted alkyl, aryl or heterocyclic radical, and the groups $R_1$ and $R_2$, together with the nitrogen atom to which they are bonded, can form a ring, which comprises coupling a diazonium salt of the formula

in which Ar is as defined above and $X^{\ominus}$ is an anion, with dimeric malonodinitrile to give an intermediate of the formula

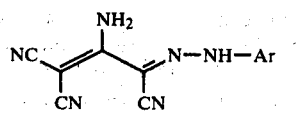

in which Ar is as defined above, and cyclising this intermediate with an alcohol or thioalcohol of the formula ROH or RSH or an amine of the formula

in which formulae R, $R_1$ and $R_2$ are as defined above, it being necessary for the amine to be present in the form of the ammonium salt during the reaction.

Ar can be any desired substituted or unsubstituted phenyl, naphthyl or aromatic heterocyclic radical, for example one of the radicals which can be used for the preparation of azo dyes.

Preferably, Ar is a substituted or unsubstituted phenyl radical or sulfur-containing and/or nitrogen-containing aromatic heterocyclic radical, it being possible for the phenyl radical to carry as substituents one or more halogen atoms or nitro, cyano, $C_1$-$C_4$-alkyl, $C_1$-$C_4$-alkoxy, m- or p-carboxyl, aryloxy, $C_1$-$C_4$-alkoxycarbonyl, sulfonamide, carboxamide, acyl, acylamino or phenylazo groups and for the phenyl nucleus in the phenylazo groups to be substituted by chlorine, nitro, cyano, $C_1$-$C_4$-alkyl, $C_1$-$C_4$-alkoxy, $C_1$-$C_4$-alkoxycarbonyl or sulfonamide groups. In a particularly preferred embodiment Ar is an unsubstituted phenyl radical or a 4-nitrophenyl, 2-chloro-4-nitrophenyl, 2-cyano-4-nitrophenyl, 2,4-dinitrophenyl, 2-chloro-4,6-dinitrophenyl or 3- or 4-carboxyphenyl radical.

If Ar is a heterocyclic radical, it is in particular a thiazole, thiophen, imidazole, pyridine, indazole, pyrazole, triazole, benztriazole, benzthiazole, thiadiazole, isothiazole or benzisothiazole radical and these radicals can be substituted by one or more nitro, chlorine, cyano, $C_1$-$C_4$-alkyl or $C_1$-$C_4$-alkoxy groups.

Alcohols thioalcohols or amines of the formulae ROH, RSH or

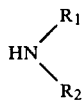

respectively which can be employed in the process according to the invention are aliphatic or aromatic alcohols, thioalcohols or amines, and aromatic compounds are also to be understood to include heterocyclic aromatic compounds.

The alcohols or thioalcohols can be primary, secondary or tertiary monohydric or polyhydric alcohols or thioalcohols and the amines can be primary or secondary amines and these compounds can be unsubstituted or substituted.

Examples of suitable alcohols and thioalcohols are: methyl alcohol, ethyl alcohol, propyl alcohol, isopropyl alcohol, butyl alcohol, isobutyl alcohol, amyl alcohol, isoamyl alcohol, octyl alcohol, cyclohexyl alcohol, benzyl alcohol, 4-chlorobenzyl alcohol, 4-methoxybenzyl alcohol, 3-methoxybenzyl alcohol, 2-methoxyethylalcohol and 2-(2-methoxyethoxy)-ethyl alcohol or the corresponding thioalcohols, and also phenol or thiophenol, which are unsubstituted or substituted by, for example, one or more alkyl, alkoxy, halogen or nitro groups, and also heterocyclic aromatic alcohols or thioalcohols, for example 2-, 3- or 4-hydroxypyridine, 2- or 4-mercaptopyridine and hydroxy- or mercapto-pyrimidine, -quinoline, -benzimidazole or -benzothiazole.

Preferably, the alcohols or thioalcohols of the formula $R_3OH$ or $R_3SH$ which are used are those in which $R_3$ is a straight-chain or branched, substituted or unsubstituted $C_1$-$C_8$ alkyl group or a substituted or unsubstituted phenyl group.

Amongst these, suitable compounds are, in particular, the thioalcohols of the formula $R_4SH$ and especially the alcohols of the formula $R_4OH$, in which $R_4$ is a straight-chain or branched $C_1$-$C_5$-alkyl group, which can carry a phenyl, $C_1$-$C_4$ alkoxy, hydroxyl, carboxyl or alkoxyalkoxy radical having a total of 2-8 C atoms.

Suitable amines are, for example: aliphatic amines, for example methylamine, ethylamine, dimethylamine, n-, sec.- or tert.-butylamine, amylamine, octylamine, dipropylamine or diisopropylamine, cyclohexylamine, cyclooctylamine and also pyrrolidine, piperidine, morpholine, thiomorpholine, piperazine, aniline, N-alkylanilines, for example N-methylaniline, naphthylamine, aminopyridine, aminopyrazine and aminopyrimidine, and all of these amines can be substituted, for example by alkoxy, hydroxyl, carboxyl or phenyl, for example benzylamine, 2-methoxyethylamine or 4-aminobutyric acid.

Amines preferably employed are those of the formula

in which $R_6$ and $R_7$ independently of one another are hydrogen, a straight-chain or branched $C_1$-$C_8$ alkyl group, which can be substituted by alkoxy, hydroxyl, carboxyl or phenyl, or a $C_5$-$C_7$ cycloalkyl group or a phenyl group, or in which $R_6$ and $R_7$ together with the nitrogen atom to which they are bonded form a pyrrolidine, piperidine, morpholine, thiomorpholine or piperazine ring.

In the process according to the invention, these amines must be in the form of ammonium salts and this is preferably achieved by carrying out the reaction of these amines with the intermediate obtained by coupling the diazonium salt with dimeric malonodinitrile in the presence of acids, preferably of organic carboxylic acids, for example acetic acid or butyric acid but in particular benzoic acid or propionic acid. The acid is employed in an amount which is equivalent to the amine or preferably in excess.

The addition of acid is superfluous in those cases in which the amine is in the form of an inner salt, for example in the case of aminocarboxylic acids, or if the above-mentioned intermediate contains an acid group.

In some cases it is also advantageous to add acid when reacting the intermediate with an alcohol or thioalcohol.

In some cases the yield and/or the composition of the reaction products can be influenced by the nature and amount of acid.

The process according to the invention is carried out by first preparing a diazonium salt of the formula

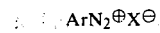

in which Ar is a substituted or unsubstituted phenyl, naphthyl or heterocyclic radical and $X^-$ is an anion, for example a chloride or sulfate anion, in a known manner and coupling this with dimeric malonodinitrile to give an intermediate of the formula

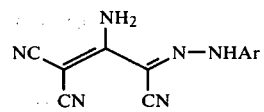

These intermediates can exist in several tautomeric forms. In order to simplify the description, only one tautomeric form is shown in each case. However, it should be expressly pointed out that the entire description, including the claims, always relates to all of these tautomeric forms.

The coupling reaction is preferably carried out at a temperature of about 0°-30° C. and especially 5°-10° C. and at a pH value of preferably 1 to 7. The coupling reaction is preferably carried out in water, but it can also be carried out in a mixture of water and an organic solvent, for example ethanol.

The resulting intermediates of the formula

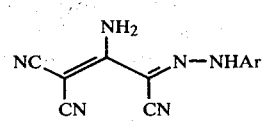

in which Ar is a substituted or unsubstituted phenyl, naphthyl or aromatic heterocyclic radical, are novel. Ar is preferably a substituted or unsubstituted phenyl radical or sulfur-containing and/or nitrogen-containing aromatic heterocyclic radical, and the phenyl radical can carry, as substituents, one or more halogen atoms or nitro, cyano, $C_1$-$C_4$-alkyl, $C_1$-$C_4$-alkoxy, m- or p-carboxyl, aryloxy, $C_1$-$C_4$-alkoxycarbonyl, sulfonamide, carboxamide, acyl, acylamino or phenylazo groups and the phenyl nucleus in the phenylazo groups can be substituted by chlorine, nitro, cyano, $C_1$–$C_4$-alkyl, $C_1$–$C_4$-alkoxy, $C_1$–$C_4$-alkoxycarbonyl or sulfonamide groups. In particularly preferred intermediates Ar is an unsubstituted phenyl radical or a 4-nitrophenyl, 2-chloro-4-nitrophenyl, 2-cyano-4-nitrophenyl, 2,4-dinitrophenyl, 2-chloro-4,6-dinitrophenyl or 3- or 4-carboxyphenyl radical.

If Ar is a heterocyclic radical, it is in particular a thiazole, thiophen, imidazole, pyridine, indazole, pyrazole, triazole, benztriazole, benzthiazole, thiadiazole, isothiazole or benzisothiazole radical, and these radicals can be substituted by one or more nitro, chlorine, cyano, $C_1$–$C_4$-alkyl or $C_1$–$C_4$-alkoxy groups.

The intermediates described above can be isolated and purified in a conventional manner prior to further use. However, it is also possible to subject the reaction solutions in which the intermediates have been formed to further processing direct to give azo dyes. (One-pot process; preferred process variant).

The cyclisation of the intermediates with an alcohol, thioalcohol or amine is carried out in water, inert solvents, for example nitrobenzene, toluene, xylene, tetralin, diethylene glycol dimethyl ether and the like, or in an excess of the particular alcohol or thioalcohol. The use of water has the advantage that the moist intermediates or aqueous suspensions of the intermediates can be employed without isolating and drying these products. A particular advantage when the reaction is carried out in water is that it is possible to carry out the coupling reaction and cyclisation as a one-pot reaction.

The cyclisation is carried out at about 50° to 200° C. and preferably 60° to 180° C. if it is effected under anhydrous conditions and preferably at 60°–100° C. in water and, depending on the reaction conditions and the nature of the components employed, requires between about 5 minutes and several days.

The azo dyes obtained by the process according to the invention are those of the formula

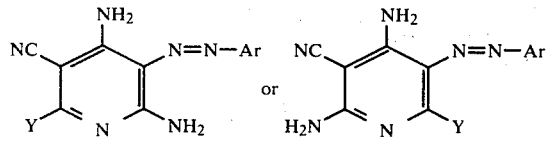

or their mixtures, in which Ar is a substituted or unsubstituted phenyl, naphthyl or aromatic heterocyclic radical and Y is a group of the formula —O—R, —S—R or

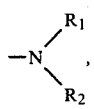

in which R is a substituted or unsubstituted alkyl, aryl or heterocyclic radical and $R_1$ and $R_2$ independently of one another are hydrogen or a substituted or unsubstituted alkyl, aryl or heterocyclic radical, and the groups $R_1$ and $R_2$ together with the nitrogen atom to which they are bonded can form a ring.

Amongst these dyes, those in which the azo group is located in the p-position relative to the Y grouping are known in some cases, for example from German Offenlegungsschrift No. 2,263,007, whilst the dyes in which these groups are located in the o-position, and also the dye mixtures, are novel.

Amongst the novel dyes, preferred dyes are those of the formula

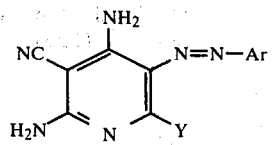

in which Ar is a substituted or unsubstituted phenyl radical or a sulfur-containing and/or nitrogen-containing aromatic heterocyclic radical. In particular Ar is a phenyl radical which can carry one or more halogen atoms or nitro, cyano, $C_1$–$C_4$-alkyl, $C_1$–$C_4$-alkoxy, m- or p-carboxyl, aryloxy, $C_1$–$C_4$-alkoxycarbonyl, sulfonamide, carboxamide, acyl, acylamino or phenylazo groups, and the phenyl nucleus in the phenylazo groups can be substituted by chlorine, nitro, cyano, $C_1$–$C_4$-alkyl, $C_1$–$C_4$-alkoxycarbonyl or sulfonamide groups, and is especially a phenyl radical, a 4-nitrophenyl, 2-chloro-4-nitrophenyl, 2-cyano-4-nitrophenyl, 2,4-dinitrophenyl or 2-chloro-4,6-dinitrophenyl radical or a 3- or 4-carboxyphenyl radical.

Further preferred dyes are those in which Ar is a thiazole, thiophen, imidazole, pyridine, indazole, pyrazole, triazole, benztriazole, benzthiazole, thiadiazole, isothiazole or benzisothiazole radical, which can be substituted by one or more nitro, chlorine, cyano, $C_1$–$C_4$-alkyl or $C_1$–$C_4$-alkoxy groups.

In preferred dyes, Y is a radical of the formula $OR_3$ or $SR_3$, in which $R_3$ is a straight-chain or branched, substituted or unsubstituted $C_1$–$C_8$ alkyl group or a substituted or unsubstituted phenyl group.

Y is preferably a radical of the formula —$SR_4$ or especially —$OR_4$, in which $R_4$ is a straight-chain or branched $C_1$–$C_5$-alkyl group, which can carry a phenyl, $C_1$–$C_4$-alkoxy, hydroxyl or carboxyl radical or an alkoxyalkoxy radical having a total of 2–8 C atoms.

Particularly valuable dyes are, in addition, those in which Y is a radical of the formula

in which $R_6$ and $R_7$ independently of one another are hydrogen, a straight-chain or branched $C_1$–$C_8$-alkyl group, which can be substituted by alkoxy, hydroxyl, carboxyl or phenyl, or a $C_5$–$C_7$-cycloalkyl group or a phenyl group, or in which $R_6$ and $R_7$ together with the nitrogen atom to which they are bonded form a pyrrolidine, piperidine, morpholine, thiomorpholine or piperazine ring.

Amongst these, preferred dyes are those of the formula

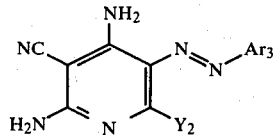

in which $Ar_3$ is a phenyl radical or a 4-nitrophenyl, 2-chloro-4-nitrophenyl, 2-cyano-4-nitrophenyl, 2,4-dinitrophenyl, 2-chloro-4,6-dinitrophenyl or 3- or 4-carboxyphenyl radical and $Y_2$ is a radical of the formula —$OR_4$ or —$SR_4$, in which $R_4$ is a straight-chain or branched $C_1$–$C_5$-alkyl group, which can carry a phenyl, $C_1$–$C_4$-alkoxy, hydroxyl or carboxyl radical or an alkoxyalkoxy radical having a total of 2–8 C atoms, and also the dyes of the formula

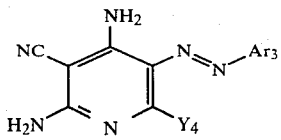

in which $Ar_3$ is a phenyl radical or a 4-nitrophenyl, 2-chloro-4-nitrophenyl, 2-cyano-4-nitrophenyl, 2,4-dinitrophenyl, 2-chloro-4,6-dinitrophenyl or 3- or 4-carboxyphenyl radical and $Y_4$ is a radical of the formula

in which $R_6$ and $R_7$ independently of one another are hydrogen, a straight-chain or branched $C_1$–$C_8$-alkyl group, which can be substituted by alkoxy, hydroxyl, carboxyl or phenyl, or a $C_5$–$C_7$-cycloalkyl group or a phenyl group, or in which $R_6$ and $R_7$ together with the nitrogen atom to which they are bonded form a pyrrolidine, piperidine, morpholine, thiomorpholine or piperazine ring.

The water-insoluble dyes obtainable according to the invention are processed to dye preparations in a generally known manner, for example by grinding in the presence of dispersing agents and/or fillers. Dyeing, padding or printing from a so-called long or short liquor can be carried out with the preparations, which are dried in vacuo if desired, after adding a greater or lesser amount of water.

The uptake of the dyes from an aqueous suspension on textile material made of wholly synthetic or semisynthetic, hydrophobic, high-molecular weight organic materials is excellent. The dyes are particularly suitable for dyeing and printing textile material made of cellulose 2½-acetate, cellulose triacetate and synthetic polyamides and especially textile material made of aromatic polyesters, for example those of terephthalic acid and ethylene glycol or 1,4-dimethylolcyclohexane and fibres of copolymers of terephthalic acid and isophthalic acid and ethylene glycol.

For dyeing from aqueous liquors, the dyes are advantageously employed in a finely divded form and dyeing is carried out in the presence of dispersing agents or wetting agents or in the presence of a combination of different wetting agents and dispersing agents.

In order to obtain intense dyeings on polyethylene terephthalate fibres from an aqueous dye liquor it is appropriate to add a carrier to the dye liquor or to carry out the dyeing process under pressure at a temperature above 100° C. Suitable carriers are, for example, benzenedicarboxylate, o-phenylphenol, chlorobenzene or an alkylnaphthalene.

If the dye is applied by padding or printing, the polyester fabric, advantageously after drying, is heated, for example in steam or warm air, to temperatures above 100° C., for example to temperatures of between 180° and 210° C.

The dyeings obtained according to the invention can be subjected to an after-treatment, for example by heating with an aqueous solution of a non-ionic detergent.

Cellulose 2½-acetate fibres are preferably dyed at temperatures of 80°–85° C., whilst cellulose triacetate fibres are advantageously dyed at the boiling point of the dye liquor. The use of carriers or swelling agents is superfluous when dyeing cellulose 2½-acetate or polyamide fibres.

In many cases the colour yield is improved if dye mixtures such as are frequently obtained from the process according to the invention are used. Preferably, each component is present in the mixtures in an amount of at least 5% by weight.

On synthetic textile material, the dyes according to the invention give deep, luminous dyeings with very good general fastness properties. The stability to heat-curing, the fastness to thermofixing, pleating, offgas, cross-dyeing, drycleaning and chlorine and also the good wet fastness properties, for example towards water, seawater, washing and perspiration, and the good fastness to light are to be singled out. Furthermore, the dyes are distinguished by a good absorption and build-up on the said material.

The dyes show good affinity for the fibre and a good degree of exhaustion. The dyeings are fast to oiling agents, ozone, flue gas, rubbing and solvents and the reserve on cotton and the stability to high temperatures are good.

It is also possible to use the water-insoluble dyes according to the invention for spin dyeing (bulk dyeing) of polyamides, polyesters and polyolefins. The polymers intended for dyeing are preferably dyed in the form of powders, grains or flocks, as they come from the spinning solution, or are mixed in the molten state with the dye, which is introduced in the dry state or in the form of a dispersion or a solution in a solvent, which can be volatile. After the dye has been uniformly dispersed in the solution or melt of the polymer, the mixture can be processed in a known manner by casting, shaping or extruding to give fibres, yarns, monofilaments, films and the like.

The following examples illustrate the invention. The temperatures are in degrees centigrade and the parts and percentages are by weight.

EXAMPLE 1

9.83 g of aniline are dissolved in 60 ml of 4 N hydrochloric acid and a solution of 7.25 g of sodium nitrite in 25 ml of water is added slowly at 0° to 5°. After the diazotisation has ended, the pH is adjusted to 6.1 with about 3.35 g of sodium bicarbonate. 15.4 g of the sodium salt of 2-amino-1,1,3-tricyano-1-propene, dissolved in 200 ml of water, are now allowed to run in dropwise at 5° to 10° and the pH rises to about 6.4 by the end of the reaction. The precipitate is stirred for a further ½ hour at 5° to 10° and is filtered off through a G4 glass suction filter and washed with water. After drying at 50° in vacuo, this yields 22.4 g of 2-amino-1,1,3-tricyano-1-propen-3-one phenylhydrazone, which corresponds to 94.9% of theory (based on the sodium salt of 2-amino-1,1,3-tricyano-1-propene employed). The product decomposes at about 195° (recrystallisation from acetone).

Analysis for $C_{12}H_8N_6$ (molecular weight=236.24):

|  | C | H | N |
| --- | --- | --- | --- |
| calculated: | 61.01 | 3.42 | 35.58 |

-continued

| | C | H | N |
|---|---|---|---|
| found: | 60.97 | 3.58 | 35.21 |

EXAMPLE 2

13.8 g of 4-nitroaniline are dissolved in 25 ml of water and 25 ml of concentrated hydrochloric acid. 6.9 g of sodium nitrite, dissolved in 40 ml of water, are now allowed to run in slowly dropwise at 0° to 5° and the mixture is stirred for a further 2 hours at 0° to 5°. This diazonium salt solution is introduced slowly into a solution, which is kept at 5° to 10°, of 15.4 g of the sodium salt of 2-amino-1,1,3-tricyano-1-propene in 200 ml of water. The pH is kept between 3 and 7 with 10 N sodium hydroxide solution. After all of the diazonium salt solution has been introduced, the pH of the suspension is adjusted to 4 with 10 N sodium hydroxide solution, the suspension is stirred for a further one hour and filtered through a G4 glass suction filter and the residue is washed with water of pH 4. After drying at 50°, this yields 27.0 g of 2-amino-1,1,3-tricyano-1-propen-3-one 4-nitrophenylhydrazone, which corresponds to 96.1% of theory (based on the sodium salt of 2-amino-1,1,3-tricyano-1-propene employed). The product decomposes above about 250° (recrystallisation from acetone).

Analysis for $C_{12}H_7N_7O_2$ (molecular weight = 281.24):

| | C | H | N | O |
|---|---|---|---|---|
| calculated: | 51.25 | 2.51 | 34.87 | 11.38 |
| found: | 51.35 | 2.59 | 35.05 | |

EXAMPLE 3

22.1 g of moist 83% 2,4-dinitroaniline are introduced slowly at 35° to 40° into 40 g of 96% sulfuric acid at a rate such that a clear solution forms. 31.4 g of 42% nitrosylsulfuric acid are then added dropwise at 0°, with stirring, and the reaction mixture is stirred for a further 2 hours and introduced into a solution of 15.4 g of the sodium salt of 2-amino-1,1,3-tricyano-1-propene in 600 ml of water, at 5° to 10°, a pH of 3 to 7 being maintained by adding concentrated sodium hydroxide solution dropwise at the same time. After the coupling reaction has ended the pH is adjusted to 6.5, the reaction mixture is stirred for a further 15 minutes and filtered through a G4 glass suction filter and the residue is washed with water and dried at 60°. This yields 30.2 g of 2-amino-1,1,3-tricyano-1-propen-3-one 2,4-dinitro-phenylhydrazone, which corresponds to 92.6% of theory (based on the sodium salt of 2-amino-1,1,3-tricyano-1-propene employed). The product decomposes above about 175° (recrystallisation from acetone).

Analysis for $C_{12}H_6N_8O_4$ (molecular weight = 326.23):

| | C | H | N | O |
|---|---|---|---|---|
| calculated: | 44.18 | 1.86 | 34.35 | 19.62 |
| found: | 44.28 | 2.00 | 34.37 | |

EXAMPLE 4

6.85 g of 4-amino-benzoic acid are dissolved in 160 ml of ethanol. 28 ml of concentrated hydrochloric acid are added dropwise at 20°, with cooling. After stirring for a further 15 minutes, 3.45 g of sodium nitrate, dissolved in 4 ml of water, are added dropwise at 15°-20°. After stirring for a further 2 hours, a suspension of 7.7 g of the sodium salt of 2-amino-1,1,3-tricyano-1-propene in 20 ml of $H_2O$ is added dropwise and the pH of the mixture is slowly adjusted to 4 with concentrated sodium hydroxide solution. After the coupling reaction has ended, the pH is again adjusted to 1 and the batch is poured onto 500 ml of ice. The precipitate is filtered off and washed with 400 ml of dilute hydrochloric acid with a pH of 1. After drying at 50°, this yields 13.0 g of 2-amino-1,1,3-tricyano-1-propen-3-one 4-carboxy-phenylhydrazone, which corresponds to 92.8% of theory (based on 2-amino-1,1,3-tricyano-1-propene employed). Melting point > 300°.

EXAMPLE 5

11.3 g of 2-chloro-4,6-dinitroaniline are introduced in the course of 1 hour at 20°-25° into a prepared mixture of 15.5 g of 40-42% nitrosylsulfuric acid and 30 ml of 98% sulfuric acid. The mixture is then stirred for further 2 hours at 20-25°.

The diazonium salt solution prepared in this way is now introduced in portions into a solution of 7.7 g of the sodium salt of 2-amino-1,1,3-tricyano-1-propene in 300 ml of water, the portions introduced being such that a pH of 2 is obtained and the pH then being readjusted to 5 with concentrated sodium hydroxide solution after the addition of each portion. After all of the diazonium salt solution has been added, the pH of the suspension is adjusted to 1 with concentrated hydrochloric acid and the suspension is stirred for 15 minutes. The precipitate is filtered off and good suction is applied to the material on the filter. The residue is stirred into 1 l of dilute hydrochloric acid with a pH of 1, the mixture is filtered and the material on the filter is washed with about 1 l of dilute hydrochloric acid with a pH of 1 and good suction is applied. After drying at 40°-50°, 16.3 g (90.4% of theory) of 2-amino-1,1,3-tricyano-1-propen-3-one-2-chloro-4,6-dinitrophenylhydrazone are obtained. Melting point: decomposition above about 148°.

Analysis for $C_{12}H_5ClN_8O_4$ (molecular weight = 360.68):

| | C | H | Cl | N | O |
|---|---|---|---|---|---|
| calculated: | 39.96 | 1.40 | 9.83 | 31.07 | 17.74 |
| found: | 40.24 | 1.34 | 9.92 | 30.87 | |

EXAMPLE 6

8.65 g of 2-chloro-4-nitro-aniline are introduced into 20 g of 98% sulfuric acid in the course of 30 minutes at a rate such that the temperature does not exceed 40°. After stirring for a further 30 minutes at 20°, the mixture is cooled to 0°. 15.5 g of 41% nitrosylsulfuric acid are added dropwise at 0°-5° and the mixture is then stirred for a further 2 hours at 25°. This diazonium solution and concentrated sodium hydroxide solution are now alternately added dropwise to a prepared mixture of 7.7 g of the sodium salt of 2-amino-1,1,3-tricyano-1-propene in 300 ml of water in such a way that the pH remains between 2 and 5. Finally, concentrated sodium hydroxide solution is added dropwise until the pH is 4.5. After stirring for 15 minutes, the pH is adjusted to 1 with concentrated hydrochloric acid and the precipitate is filtered off and washed with about 1 l of dilute hydrochloric acid with a pH of 1 and good suction is applied to the material on the filter. After drying at 50°, this yields 15.0 g of 2-amino-1,1,3-tricyano-1-propen-3-one 2-chloro-4-nitro-phenylhydrazone, which corresponds to 95.1% of theory (based on 2-amino-1,1,3-tricyano-1-propene employed). Melting point: decomposition above about 145°.

EXAMPLE 7

1.18 g of 2-amino-1,1,3-tricyano-1-propen-3-one phenylhydrazone in 150 ml of methanol are refluxed for 8 hours. After distilling off the solvent, the residue is introduced, as finely ground material, onto a G4 glass suction filter and washed with cold methanol. After drying the residue, 590 mg (=44% of theory) of the dye which has the formula given below and a melting point of 224°-5° (recrystallisation from dioxan) are obtained.

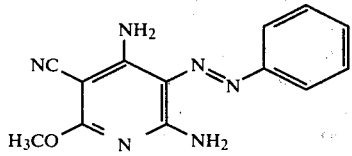

Analysis for $C_{13}H_{12}N_6O$ (molecular weight = 268.28):

|  | C | H | N | O |
|---|---|---|---|---|
| calculated: | 58.20 | 4.51 | 31.33 | 5.96 |
| found: | 58.24 | 4.59 | 31.33 |  |

A further 90 mg = 6% of theory of the above dye result on filtering the evaporated mother liquor through 30 g of silica gel 60 F254 (Merck), in ethylene chloride as the solvent. The dye dyes polyester fibres in yellow shades with good fastness properties.

EXAMPLE 8

1.18 g of 2-amino-1,1,3-tricyano-1-propen-3-one phenylhydrazone and 2.07 g of piperidinium benzoate in 10 ml of diethylene glycol dimethyl ether are stirred at 120° for 45 minutes. 20 ml of water are allowed to run in dropwise and the precipitate is filtered off and washed with water. The residue is filtered, in ethylene chloride as the solvent, through 100 g of silica gel 60 F254 (Merck). After evaporating, 752 mg (47% of theory) of the dye which has the formula given below and a melting point of 171°-2° (recrystallisation from ethylene chloride) are obtained:

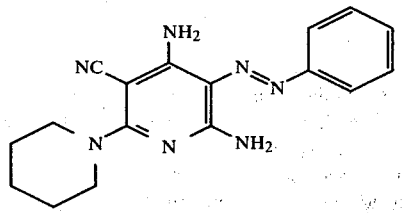

Analysis for $C_{17}H_{19}N_7$ (molecular weight = 321.39):

|  | C | H | N |
|---|---|---|---|
| calculated: | 63.53 | 5.96 | 30.51 |
| found: | 63.39 | 5.98 | 30.16. |

EXAMPLE 9

1.43 g of 2-amino-1,1,3-tricyano-1-propen-3-one 4-nitrophenylhydrazone are introduced at 130° into a solution of 1 g of cyclohexylamine, 1.05 g of propionic acid and 10 ml of diethylene glycol dimethyl ether. After 20 minutes, the mixture is allowed to cool, 30 ml of water are added dropwise and the precipitate is filtered off using a G4 glass suction filter and washed with water. The residue is chromatographed, in ethylene chloride as the solvent, through a column packed with 200 g of silica gel 60 F254 (Merck). 74 mg (3.9% of theory) of the dye which has the formula given below and a melting point of 281°-2° (recrystallisation from ethylene chloride) are obtained:

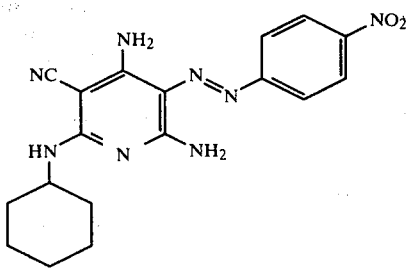

Analysis for $C_{18}H_{20}N_8O_2$ (molecular weight = 380.41):

|  | C | H | N | O |
|---|---|---|---|---|
| calculated: | 56.83 | 5.30 | 29.46 | 8.41 |
| found: | 56.89 | 5.44 | 29.31 |  |

Further elution with ethylene chloride yields 1.601 g (84.1% of theory) of the dye which has the formula given below (decomposition temperature >260°; recrystallisation from ethylene chloride):

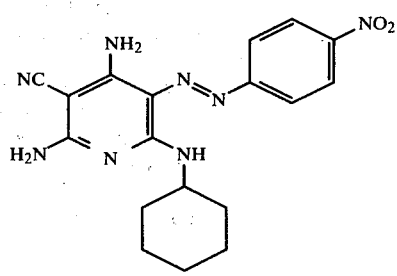

Analysis for $C_{18}H_{20}N_8O_2$ (molecular weight = 380.41):

|  | C | H | N | O |
|---|---|---|---|---|
| calculated: | 56.83 | 5.30 | 29.46 | 8.41 |
| found: | 56.60 | 5.40 | 29.40 |  |

The dyes dye polyester fibres in orange shades with good fastness properties.

EXAMPLE 10

1.43 of 2-amino-1,1,3-tricyano-1-propen-3-one 4-nitrophenylhydrazone are introduced at 135° to 140° into a solution of 1.07 g of benzylamine, 1.05 of propionic acid and 10 ml of diethylene glycol dimethyl ether. After 30 minutes the mixture is allowed to cool and 30 ml of water are added dropwise. The precipitate is filtered off and washed with water. The residue is chromatographed, in ethylene chloride as the solvent, through a column packed with 200 g of silica gel 60 F254 (Merck). 0.932 g (48.0% of theory) of the dye which has the formula given below and a melting point of 286°-7° (recrystallisation from ethylene chloride) is obtained:

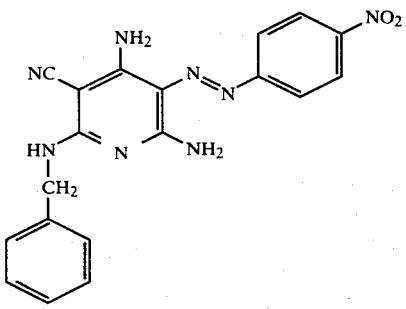

Analysis for $C_{19}H_{16}N_8O_2$ (molecular weight=388.39):

| | C | H | N | O |
|---|---|---|---|---|
| claculated | 58.76 | 4.15 | 28.85 | 8.24 |
| found: | 58.75 | 4.12 | 28.60 | |

Further elution with ethylene chloride yields 0.427 g (22% of theory) of the dye which has the formula given below and a melting point of 261°-2° (recrystallisation from ethylene chloride):

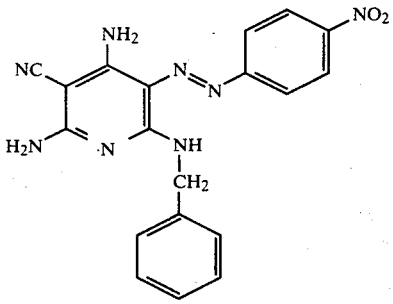

Analysis for $C_{19}H_{16}N_8O_2$ (molecular weight=388.39):

| | C | H | N | O |
|---|---|---|---|---|
| calculated: | 58.76 | 4.15 | 28.85 | 8.24 |
| found: | 58.61 | 4.19 | 28.84 | |

EXAMPLE 11

1.63 g of 2-amino-1,1,3-tricyano-1-propen-3-one 2,4-dinitrophenylhydrazone are introduced at 120° to 125° into a solution of 0.87 g of morpholine, 1.05 g of propionic acid and 5 ml of diethylene glycol dimethyl ether. After 15 minutes the mixture is allowed to cool and 10 ml of water are added dropwise and the residue is filtered off and washed with water. Recrystallisation of the residue from acetone and chromatography of the mother liquor through a column packed with 150 g of silica gel 60 F254, in toluene:acetone=3:1 as the solvent, yields 1.226 g (59% of theory) of the dye which has the formula given below and a melting point of 222°-224° (recrystallisation from ethylene chloride):

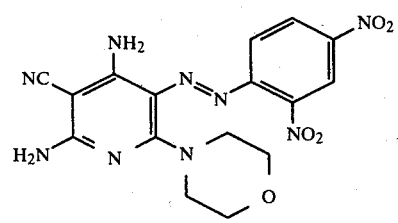

Analysis for $C_{16}H_{15}N_9O_5$ (molecular weight=413.35):

| | C | H | N | O |
|---|---|---|---|---|
| calculated: | 46.49 | 3.66 | 30.50 | 19.35 |
| found: | 46.49 | 3.68 | 30.36 | 19.32 | and 64 mg (3.1% of theory) of the dye which has the formula given below and a melting point of 278°-9° (decomposition) (recrystallisation from ethylene chloride):

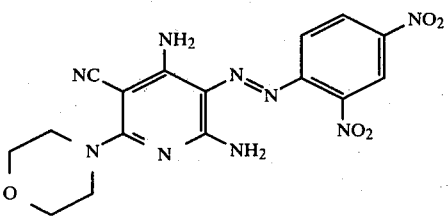

Analysis for $C_{16}H_{15}N_9O_5$ (molecular weight=413.35):

| | C | H | N | O |
|---|---|---|---|---|
| calculated: | 46.49 | 3.66 | 30.50 | 19.35 |
| found: | 46.59 | 3.77 | 30.25 | |

The dyes dye polyester fibres in red colour shades.

EXAMPLE 12

1.406 g of 2-amino-1,1,3-tricyano-1-propen-3-one 4-nitrophenylhydrazone are introduced at 120° to 125° into a solution of 0.37 g of propionic acid in 10 ml of benzyl alcohol. After stirring for 45 minutes at 125° the mixture is allowed to cool, 5 ml of methanol are added and the mixture is cooled to 0°. The precipitate is filtered off and washed with twice 5 ml of methanol. After drying at 80°, 1.633 g (83.9% of theory) of the dye which has +he formula given below and a melting point of 246°-7° (recrystallization from methylene chloride) are obtained:

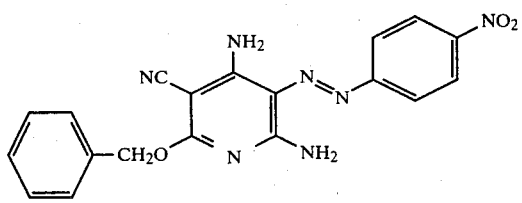

Analysis for C$_{19}$H$_{15}$N$_7$O$_3$ (molecular weight = 39.38):

|  | C | H | N | O |
|---|---|---|---|---|
| calculated: | 58.61 | 3.88 | 25.18 | 12.33 |
| found: | 58.78 | 3.96 | 25.30 |  |

The dyes dye polyester fibres in yellow colour shades with good fastness properties.

EXAMPLE 13

1,406 g of 2-amino-1,1,3-tricyano-1-propen-3-one 4-nitrophenylhydrazone are introduced at 120° to 125° into a solution of 122 mg of benzoic acid in 30 ml of isoamyl alcohol. After stirring for 4 hours at 120° to 125°, the solvent is distilled off in vacuo and the residue is chromatographed through a column packed with 80 g of silica gel 60 F254, in toluene as the solvent. This yields 108 mg (5.8% of theory) of the dye which has the formula given below and a melting point 200°-1° (recrystallization from methylene chloride/carbon tetrachloride):

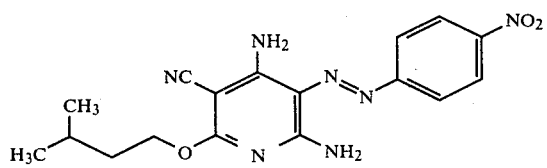

Analysis for C$_{17}$H$_{19}$N$_7$O$_3$ (molecular weight = 369.39):

|  | C | H | N | O |
|---|---|---|---|---|
| calculated: | 55.28 | 5.19 | 26.54 | 13.00 |
| found: | 55.21 | 5.23 | 26.58 |  | and 1.060 g (54.5% of theory) of the dye which has the formula given below and a melting point of 200°-1° (recrystallization from methylene chloride/carbon tetrachloride):

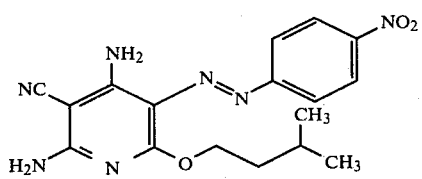

Analysis for C$_{17}$H$_{19}$N$_7$O$_3$ (molecular weight = 369.39):

|  | C | H | N | O |
|---|---|---|---|---|
| calculated: | 55.28 | 5.19 | 26.54 | 13.00 |
| found: | 55.15 | 5.20 | 26.64 |  |

The dyes dye polyester fibres in yellow colour shades with good fastness properties.

EXAMPLE 14

The procedure of Example 13 is repeated, except that 0.61 g of benzoic acid is employed in place of 122 mg of benzoic acid. Only the dye of the formula given below is obtained, in a yield of 1.51 g (82% of theory):

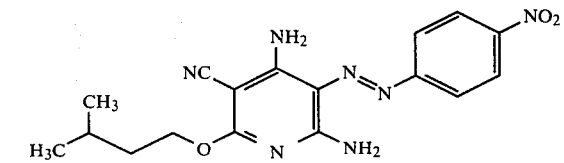

EXAMPLE 15

1,406 g of 2-amino-1,1,3-tricyano-1-propen-3-one 4-nitrophenylhydrazone are introduced in the course of 10 minutes, at 140°, into a solution of 0.35 ml of propionic acid and 5 ml of diethylene glycol monomethyl ether. After stirring for 50 minutes at 140°, the mixtures is allowed to cool to 100° and 10 ml of water are added dropwise. The precipitate is filtered off, the residue is washed with water and then dissolved in 250 ml of boiling ethylene chloride and the solution is filtered through a G4 glass suction filter. Evaporation of the filtrate yields 1.598 g (79.6% of theory) of the dye which has the formula given below and a melting point of 186°-7° (recrystallisation from ethylene chloride):

H$_3$COCH$_2$CH$_2$OCH$_2$CH$_2$O—[structure with NC, NH$_2$, N=N-C$_6$H$_4$-NO$_2$, NH$_2$]

Analysis for C$_{17}$H$_{19}$N$_7$O$_5$ (molecular weight = 401.39):

|  | C | H | N | O |
|---|---|---|---|---|
| calculated: | 50.85 | 4.77 | 24.44 | 19.94 |
| found: | 50.61 | 4.72 | 24.27 |  |

The dyes dye polyester fibres in yellow colour shades with good fastness properties.

EXAMPLE 16

1.181 g of 2-amino-1,1,3-tricyano-1-propen-3-one phenylhydrazone in 200 ml of ethanol are refluxed for 65 hours and the solvent is then distilled off. The residue is chromatographed in toluene:acetone = 3:1 as the solvent through a column packed with 80 g of silica gel 60 F 254 (Merck). This yields 891 mg (63.1% of theory) of the dye which has the formula given below and a melting point of 222°-3° (recrystallisation from acetone/toluene):

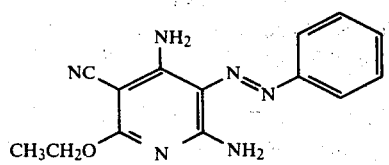

Analysis for $C_{14}H_{14}N_6O$ (molecular weight=282.31):

|  | C | H | N |
|---|---|---|---|
| calculated: | 59.57 | 5.00 | 29.77 |
| found: | 59.56 | 5.09 | 29.45 |

The dye dyes polyester fibres in yellow colour shades with good fastness properties.

EXAMPLE 17

1.181 g of 2-amino-1,1,3-tricyano-1-propen-3-one phenylhydrazone and 122 mg of benzoic acid in 5 ml of 2-methoxyethanol are refluxed for 1 hour. After distilling off the solvent, the residue is filtered, in toluene:acetone=4:1 as the solvent, through a column packed with 100 g of silica gel 60 F254 (Merck) and the filtrate is evaporated. This yields 1.287 g (82.4% of theory) of the dye which has the formula given below and a melting point of 188°-9° (recrystallisation from acetone/toluene):

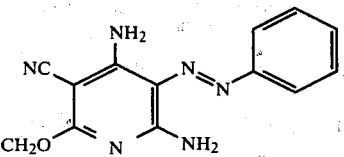

Analysis for $C_{15}H_{16}N_6O_2$ (molecular weight=312.33):

|  | C | H | N | O |
|---|---|---|---|---|
| calculated: | 57.69 | 5.17 | 26.91 | 10.25 |
| found: | 57.74 | 5.25 | 26.80 |  |

The dye dyes polyester fibres in yellow colour shades with good fastness properties.

EXAMPLE 18

1.631 g of 2-amino-1,1,3-tricyano-1-propen-3-one 2,4-dinitrophenylhydrazone are stirred at 130° in a solution of 0.33 g of propionic acid and 10 ml of benzyl alcohol for 1 hour. After cooling, 10 ml of methanol and then 10 ml of water are added dropwise, the suspension is cooled to 0° and filtered and the residue is washed cold with a mixture of 2.5 ml of methanol and 5 ml of water. After drying at 80°, this yields 1.63 g (75.0% of theory) of the dye which has the formula given below and a melting point of 257°-8° (recrystallisation from ethylene chloride):

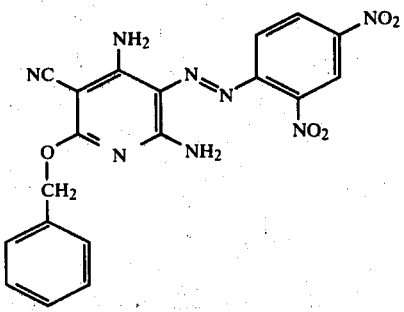

Analysis for $C_{19}H_{14}N_8O_5$ (molecular weight=434.37):

|  | C | H | N | O |
|---|---|---|---|---|
| calculated: | 52.54 | 3.25 | 25.80 | 18.42 |
| found: | 52.33 | 3.33 | 25.66 |  |

The dye dyes polyester fibres in yellow colour shades with good fastness properties.

EXAMPLE 19

1.631 g of 2-amino-1,1,3-tricyano-1-propen-3-one 2,4-dinitrophenylhydrazone are stirred at 130° in a solution of 1.0 g of cyclohexylamine, 1.05 g of propionic acid and 10 ml of diethylene glycol dimethyl ether for 10 minutes. 20 ml of water are then added dropwise and, after cooling to 20°, the precipitate is filtered off, washed with water and dried at 80°. The crude product is chromatogrphed through a column packed with 150 g of silica gel 60 F254, in ethylene chloride as the solvent. This yields 0.151 g (7.1% of theory) of the dye which has the formula given below and a melting point of 221°-2° (recrystallisation from ethylene chloride):

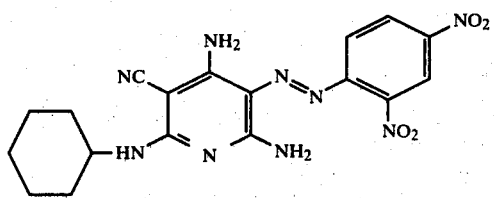

Analysis for $C_{18}H_{19}N_9O_4$ (molecular weight=425.41):

|  | C | H | N | O |
|---|---|---|---|---|
| calculated: | 50.82 | 4.50 | 29.64 | 15.04 |
| found: | 50.43 | 4.48 | 29.32 |  |

Further elution with ethylene chloride yields 1.688 g (79.3% of theory) of the dye which has the formula given below and a melting point of >275° (decomposition) (recrystallisation from ethylene chloride):

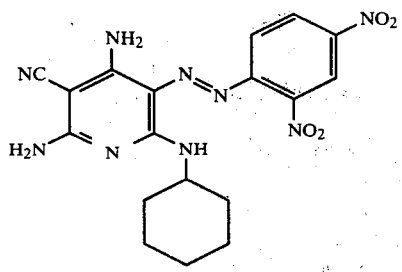

Analysis for C₁₈H₁₉N₉O₄ (molecular weight=425.41):

|  | C | H | N | O |
|---|---|---|---|---|
| calculated: | 50.82 | 4.50 | 29.64 | 15.04 |
| found: | 50.84 | 4.51 | 29.91 |  |

The dyes dye polyester fibres in red colour shades with good fastness properties.

EXAMPLE 20

1.406 g of 2-amino-1,1,3-tricyano-1-propen-3-one 4-nitrophenylhydrazone are introduced at 130° into a mixture of 10 ml of diethylene glycol dimethyl ether, 1.2 ml of benzylmercaptan and 0.37 g of propionic acid. After stirring for 15 minutes at 130°-135°, the mixture is allowed to cool to 20°, the dye is precipitated by the dropwise addition of 15 ml of water and the product, after filtering off, is washed with water. 1.96 g of crude product are obtained and after recrystallisation from acetone and column chromatography of the mother liquor on 150 g of silica gel 60 F254, in ethylene chloride as the solvent, this yields a total of 1.71 g=84.5% of the dye which has the formula given below and a melting point of 248°-9° (recrystallisation from acetone):

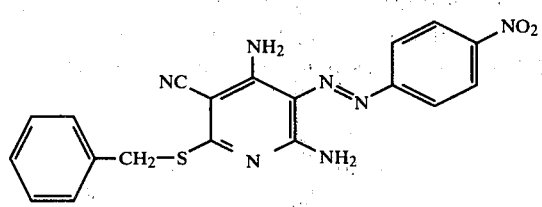

Analysis for C₁₉H₁₅N₇SO₂ (molecular weight=405.44):

|  | C | H | N | S | O |
|---|---|---|---|---|---|
| calculated: | 56.29 | 3.73 | 24.18 | 7.91 | 7.89 |
| found: | 56.27 | 3.92 | 23.97 | 7.70 |  |

The dye dyes polyester fibres in yellow colour shades with good fastness properties.

EXAMPLE 21

1.406 g of 2-amino-1,1,3-tricyano-1-propen-3-one 4-nitrophenylhydrazone are introduced at 115° into a mixture of 10 ml of diethylene glycol dimethyl ether, 1.29 g of octylamine and 1.11 g of propionic acid. After stirring for 20 minutes at 115°-120°, the mixture is allowed to cool to 20° and the product is precipitated by seeding and dropwise addition of 15 ml of water. The precipitate is filtered off and washed with water and dried and 1.93 g (94%) of crude product are thus obtained. This is chromatographed through a column packed with 200 g of silica gel 60 F254, in ethylene chloride as the solvent.

This yields 900 mg (44% of theory) of the dye which has the formula given below and a melting point of 180°-2° (recrystallisation from ethylene chloride):

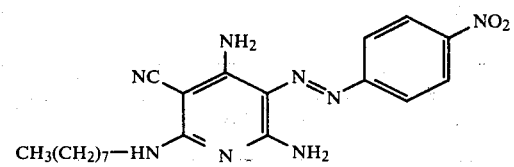

Analysis for C₂₀H₂₆N₈O₂ (molecular weight=410.48):

|  | C | H | N | O |
|---|---|---|---|---|
| calculated: | 58.52 | 6.39 | 27.30 | 7.80 |
| found: | 58.37 | 6.38 | 27.17 |  |

Further elution with ethylene chloride yields 0.551 g (27%) of the dye which has the formula given below and a melting point of 193°-4° (recrystallisation from ethylene chloride):

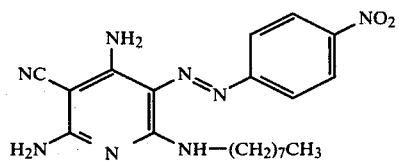

Analysis for C₂₀H₂₆N₈O₂ (molecular weight=410.48):

|  | C | H | N | O |
|---|---|---|---|---|
| calculated: | 58.52 | 6.39 | 27.30 | 7.80 |
| found: | 58.65 | 6.40 | 27.28 |  |

The dyes dye polyester fibres in orange colour shades with good fastness properties.

EXAMPLE 22

1.578 g of 2-amino-1,1,3-tricyano-1-propen-3-one 2-chloro-4-nitro-phenylhydrazone are introduced at 130° into a prepared mixture of 10 ml of diethylene glycol dimethyl ether, 1.0 g of cyclohexylamine and 1.11 g of propionic acid. After 25 minutes the mixture is allowed to cool to 80° and 20 ml of water are added dropwise. The precipitate is filtered off at 20° and washed with water. After recrystallisation of the dried residue, which weighs 1.93 g, and column chromatography of the mother liquor on 100 g of silica gel 60 F 254 (Merck), in ethylene chloride, 1.664 g (80.3% of theory) of the dye which has the formula given below and a melting point of 288°-290° (recrystallisation from ethylene chloride)

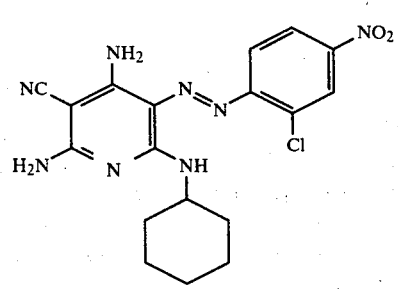

Analysis for C$_{18}$H$_{19}$ClN$_8$O$_2$ (molecular weight=414.86):

|  | C | H | Cl | N | O |
|---|---|---|---|---|---|
| calculated: | 52.11 | 4.62 | 8.55 | 27.01 | 7.71 |
| found: | 51.98 | 4.65 | 8.49 | 26.80 | 7.96 | and 102 mg (5% of theory) of the dye which has the formula given below and a melting point of 238°–241°

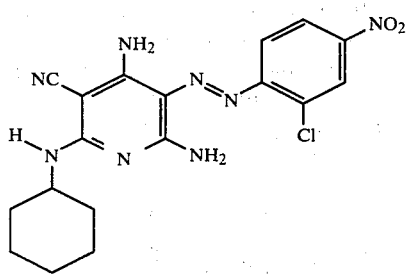

are obtained.

The dyes dye polyester fibres in orange-red colour shades with good fastness properties.

EXAMPLE 23

1.40 g of 2-amino-1,1,3-tricyano-1-propen-3-one 4-carboxyphenylhydrazone in 10 ml of diethylene glycol monomethyl ether are stirred at 150°–155° for 30 minutes. After cooling to 20°, 30 ml of water are added dropwise and the precipitate is filtered off and washed with 20 ml of water. Recrystallisation of the residue, which weighs about 1.85 g, from methanol yields 1.54 g (77% of theory) of the dye which has the formula given below and a melting point of 240°–242°:

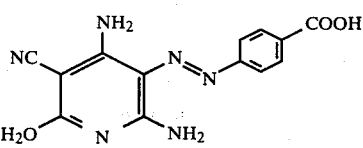

Analysis for C$_{18}$H$_{20}$N$_6$O$_5$ (molecular weight=400.40):

|  | C | H | N | O |
|---|---|---|---|---|
| calculated: | 54.00 | 5.04 | 20.99 | 19.98 |
| found: | 53.97 | 5.06 | 20.99 |  |

The dye dyes polyester fibres in yellow colour shades with good fastness properties.

EXAMPLE 24

2.118 g of 2-amino-1,1,3-tricyano-1-propen-3-one 2-chloro-4-nitrophenylhydrazone are introduced at 125° in the course of 10 minutes into a mixture of 10 ml of benzyl alcohol and 0.37 g of propionic acid. After stirring for 1 hour at 125°, the mixture is allowed to cool to about 40° and a mixture of 15 ml of methanol and 20 ml of water is added dropwise. The dye which has precipitated is filtered off at 0°, washed with 10 ml of a 1:6 mixture of methanol:water and then with water alone and dried at 60° under a high vacuum. This yields 1.705 g (80.6%) of the dye which has the formula given below and a melting point of 275°–6° (recrystallisation from acetone):

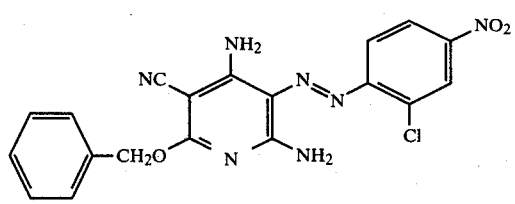

Analysis for C$_{19}$H$_{14}$ClN$_7$O$_3$ (molecular weight=423.82):

|  | C | H | Cl | N | O |
|---|---|---|---|---|---|
| calculated: | 53.85 | 3.33 | 8.37 | 23.14 | 11.33 |
| found: | 53.79 | 3.27 | 8.46 | 23.04 |  |

The dye dyes polyester fibres in orange colour shades with good fastness properties.

EXAMPLE 25

1.63 g of 2-amino-1,1,3-tricyano-1-propen-3-one 2,4-dinitrophenylhydrazone are introduced at 125° into a prepared mixture of 5 ml of diethylene glycol dimethyl ether, 0.91 ml of aniline and 1.11 g of propionic acid, with stirring. After stirring for 10 minutes at 125°–130°, the mixture is cooled to 10° and the crude dye is precipitated by the dropwise addition of 15 ml of water and filtered off. After column chromatography on 300 g of silica gel 60 F254 (Merck), in ethylene chloride as the solvent, 230 mg (11% of theory) of the dye which has the formula given below and a melting point of >140° (decomposition) are obtained. (Recrystallisation from ethylene chloride):

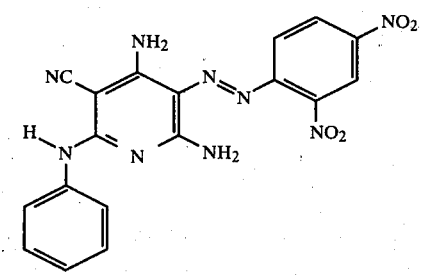

Analysis for C$_{18}$H$_{13}$N$_9$O$_4$ (molecular weight=419.36):

|  | C | H | N | O |
|---|---|---|---|---|
| calculated: | 51.55 | 3.12 | 30.06 | 15.26 |
| found: | 51.28 | 3.02 | 29.88 | |

Further elution with ethylene chloride yields 63 mg (3% of theory) of the dye which has the formula given below and a melting point of >190° (decomposition) (recrystallisation from ethylene chloride):

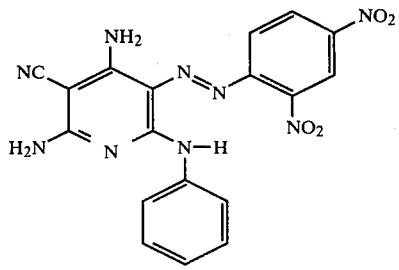

Analysis for $C_{18}H_{13}N_9O_4$ (molecular weight=419.36):

|  | C | H | N | O |
|---|---|---|---|---|
| calculated: | 51.55 | 3.12 | 30.06 | 15.26 |
| found: | 51.50 | 2.93 | 30.00 | |

The dyes dye polyester fibres in red colour shades with good fastness properties.

EXAMPLE 26

1.63 g of 2-amino-1,1,3-tricyano-1-propen-3-one 2,4-dinitrophenylhydrazone are introduced at 125° into a prepared mixture of 5 g of phenol and 0.37 g of propionic acid, with stirring, and the mixture is stirred for 1½ hours at 125°-130°. The batch is cooled to 25° and discharged into 250 ml of water and the pH of the aqueous phase is adjusted to 10 with sodium hydroxide solution. The dye, which has precipitated as crystals, is filtered off, washed well with water and, after drying, filtered, in ethylene chloride as the solvent, through 30 g of silica gel 60 F254 (Merck). This yields 1.15 g (55% of theory) of the dye which has the formula given below and a melting point of >190° (decomposition) (recrystallisation from ethylene chloride):

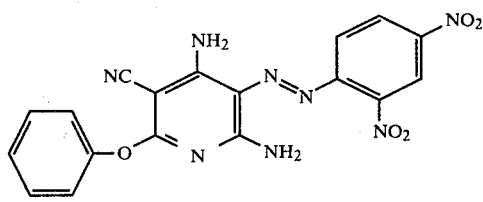

Analysis for $C_{18}H_{12}N_8O_5$ (molecular weight=420.34):

|  | C | H | N | O |
|---|---|---|---|---|
| calculated: | 51.43 | 2.88 | 26.65 | 19.03 |
| found: | 51.37 | 2.92 | 26.44 | |

The dye dyes polyester fibres in orange colour shades with good fastness properties.

EXAMPLE 27

2.21 g of 2,4-dinitro-aniline are introduced in the course of 10 minutes into 6 ml of 98% sulfuric acid and the mixture is stirred for about ½ hour until a clear solution has formed. 3.1 g of 41% nitrosylsulfuric acid are now added dropwise at 0°-5° in the course of 5 minutes. The mixture is stirred for a further 2 hours at 0°-5° and the resulting diazonium salt solution and concentrated sodium hydroxide solution are alternately added dropwise, at 0°-5°, to a prepared mixture of 1.54 g of the sodium salt of 2-amino-1,1,3-tricyano-1-propene in 20 ml of water in such a way that the pH value remains between 2 and 6. After all of the diazonium salt solution has been added, the pH is adjusted to 6 with concentrated NaOH, 2.24 g of propionic acid are then added and the batch is warmed to 80°. 2.3 ml of cyclohexylamine are now added dropwise in the course of 2 minutes at 80°-85° and the mixture is then refluxed for 20 minutes. After cooling, the dye which has precipitated is separated off and filtered, in ethylene chloride as the solvent, through 50 g of silica gel 60 F254 (Merck). After evaporating the eluate, this yields 1.89 g (44.4% of theory) of a mixture of the dyes of the following formulae, in a ratio of about 3:97:

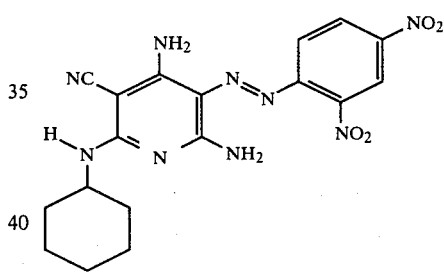

about 3%

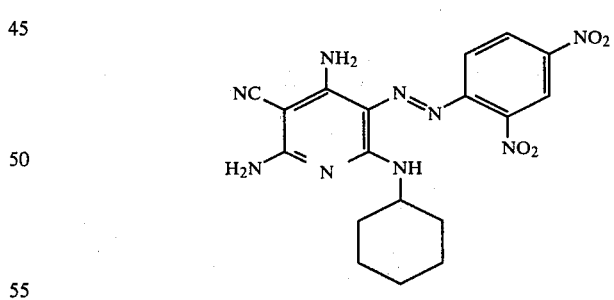

about 97%

EXAMPLE 28

0.6 ml of cyclohexylamine, 0.6 ml of propionic acid and 815 mg of 2-amino-1,1,3-tricyano-1-propen-3-one 4,6-dinitrophenylhydrazone are introduced successively into 2 ml of water. The mixture is heated, refluxed for 20 minutes and filtered hot and the material on the filter is washed with hot water. After drying at 60°-80°, this yields 965 mg (=90.7%) of a mixture of the dyes of Example 27 in a ratio of about 2:98.

EXAMPLE 29

11.3 g of 2-chloro-4,6-dinitro-aniline are introduced in the course of 1 hour, at 20°-25°, into a prepared mixture of 30 ml of 98% sulfuric acid and 15.5 g of 40% nitrosylsulfuric acid. After stirring for a further 2 hours, this solution is added dropwise at 0°-5° to a solution of the sodium salt of 2-amino-1,1,3-tricyano-1-propene in 300 ml of water. At the same time, concentrated sodium hydroxide solution is added dropwise at such a rate that the pH remains at 2-5. After the dropwise addition is complete, the pH of the batch is adjusted to 5, the mixture is stirred for a further 15 minutes, the pH is then adjusted to 1 with concentrated hydrochloric acid, the mixture is stirred for 15 minutes and filtered and the material on the filter is washed with 2 l of dilute hydrochloric acid with a pH of 1. After drying at 50°, this yields 16.3 g of 2-amino-1,1,3-tricyano-1-propen-3-one 2,4-dinitrophenylhydrazone, which corresponds to 90.4% of theory (based on 2-amino-1,1,3-tricyano-1-propene employed); this product decomposes at >148° (recrystallisation from ethyl acetate).

EXAMPLE 30

A mixture of 10 ml of diethylene glycol dimethyl ether, 1.0 g of cyclohexylamine and 1.11 g of propionic acid is warmed to 95° and 1.805 g of 2-amino-1,1,3-tricyano-1-propen-3-one 2,4-dinitro-phenylhydrazone are added. After reacting for 45 minutes at 95°-180°, the mixture is cooled to 25° and the crude product is precipitated by adding 15 ml of water and filtered off. The residue is dissolved in hot ethylene chloride and subjected to column chromatography on 350 g of silica gel 60 F245 (Merck), in ethylene chloride as the solvent. This yields 0.84 g (37%) of the dye which has the formula given below and a melting point of 271°-4° (recrystallisation from ethyl chloride):

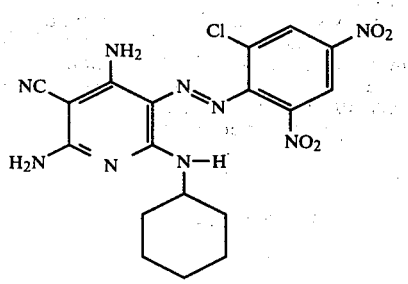

Analysis for $C_{18}H_{18}ClN_9O_4$ (molecular weight=459.85):

|  | C | H | Cl | N | O |
|---|---|---|---|---|---|
| calculated: | 47.01 | 3.94 | 7.71 | 27.41 | 13.92 |
| found: | 47.28 | 3.99 | 7.70 | 27.07 |  |

EXAMPLE 31

9.85 g of p-amino-azobenzene are introduced at 25°-30° into 30 ml of 96% sulfuric acid. After a clear solution has formed, 15.5 g of 40% nitrosylsulfuric acid are added dropwise at 0°-5° in the course of 30 minutes. After stirring for a further 1 hour, the diazonium salt solution is added dropwise at 0°-5° to a solution of 7.7 g of the sodium salt of 2-amino-1,1,3-tricyano-1-propene and a pH of 2-5 is maintained by adding concentrated sodium hydroxide solution dropwise at the same time. After the dropwise addition of the diazonium salt solution is complete, the mixture is stirred at pH 5 for 30 minutes and the pH is then adjusted to 1. The precipitate is filtered off and washed well with dilute hydrochloric acid of pH 1 and dried at 50°. This yields 16.6 g of 2-amino-1,1,3-tricyano-1-propen-3-one azobenzen-4-yl-hydrazone, which corresponds to 98% of theory (based on the 2-amino-1,1,3-tricyano-1-propene employed); this product decomposes at >220°.

EXAMPLE 32

A mixture of 4.08 g of 2-amino-1,1,3-tricyano-1-propen-3-one azobenzen-4-yl-hydrazone, 1.46 g of benzoic acid and 10 ml of n-octanol is stirred at 125°-130° for 1 hour and then diluted with 30 ml of hexane. The precipitate is filtered off, washed with hexane and dissolved in 1 l of hot ethylene chloride and the solution is filtered through 50 g of silica gel 60 F 254 (Merck). 4.58 g (81%) of the dye which has the formula given below and a melting point of 170°-2° (recrystallisation from ethylene chloride) are obtained:

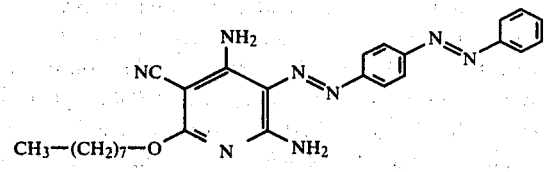

EXAMPLE 33

17.3 g of 5-amino-3-methyl-1-phenyl-pyrazole are introduced at 30°-40° into 50 ml of 70% sulfuric acid and the mixture is stirred until a clear solution forms. 31.75 g of 40% nitrosylsulfuric acid are now added dropwise at 0°-5° in the course of 1 hour. The diazonium salt solution is added dropwise at 0° to a solution of 15.4 g of the sodium salt of 2-amino-1,1,3-tricyano-1-propene in 500 ml of water and a pH of 1-5 is maintained by adding concentrated sodium hydroxide solution dropwise at the same time. The mixture is then stirred for a further ½ hour at pH 4-5, the pH is adjusted to 1 with concentrated hydrochloric acid and the product which has precipitated out is filtered off with suction. The residue is washed with a total of 5 l of dilute hydrochloric acid of pH 1 and dried at 60°. This yields 23.6 g (74.7%) of 2-amino-1,1,3-tricyano-1-propen-3-one 3-methyl-1-phenyl-pyrazol-5-yl-hydrazone, which decomposes at >245°.

EXAMPLE 34

3.05 g of benzoic acid and 7.90 g of 2-amino-1,1,3-tricyano-1-propen-3-one 3-methyl-1-phenyl-pyrazol-5-yl-hydrazone are introduced at 130° into 25 ml of isopentanol. After stirring for 2 hours at 130°-140°, the batch is cooled to 25° and discharged into 150 ml of hexane and the mixture is filtered with suction. The residue is dissolved in 500 ml of hot ethylene chloride and filtered through 70 g of silica gel 60 F 254 (Merck). 1.30 g (13%) of the dye which has the formula given below and a melting point of 192°-5° (recrystallisation from ethylene chloride) are obtained:

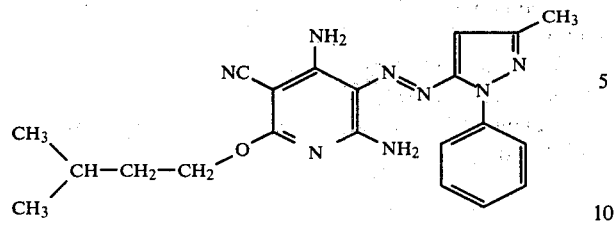

Analysis for $C_{21}H_{24}N_8O$ (molecular weight=404.48):

|  | C | H | N | O |
|---|---|---|---|---|
| calculated: | 62.36 | 5.98 | 27.70 | 3.95 |
| found: | 62.35 | 5.68 | 27.95 | 3.95 |

EXAMPLE 35

4.88 g of 3-amino-5-nitro-benzisothiazole are introduced at 10°–15° into 50 g of 85% sulfuric acid. 7.75 g of 40% nitrosylsulfuric acid are added dropwise at 0°–5° in the course of 5 minutes and the solution is stirred for a further 3 hours at 0°–5°. The suspension is added dropwise at 0° to a solution of 3.85 g of the sodium salt of 2-amino-1,1,3-tricyano-1-propene in 150 ml of water and the pH is kept at 2–5 by adding concentrated sodium hydroxide solution dropwise at the same time. The pH is now adjusted to 1 and the precipitate is filtered off and washed well with dilute hydrochloric acid of pH 1 and dried at 50°. This yields 6.6 g of 2-amino-1,1,3-tricyano-1-propen-3-one 5-nitro-benzisothiazol-3-yl-hydrazone which corresponds to 78% of theory (based on the 2-amino-1,1,3-tricyano-1-propene employed).

EXAMPLE 36

2.96 g of 2-amino-1,1,3-tricyano-1-propen-3-one 5-nitro-benzisothiazol-3-yl-hydrazone are added to a mixture of 10 ml of diethylene glycol dimethyl ether, 2.6 ml of n-hexylamine and 3.48 g of benzoic acid at 90°, and this temperature is maintained for 24 hours. After cooling to 25°, the product is precipitated with 40 ml of water and the pH of the aqueous phase is adjusted to 10 with 1 N sodium hydroxide solution and this phase is stirred for 2 hours at 25° and the product is filtered off, washed with water and dried at 40°. This yields 4.2 g (100%) of a red mixture of dyes I and II with a melting point of >50°.

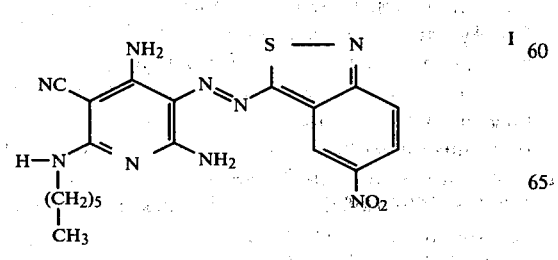

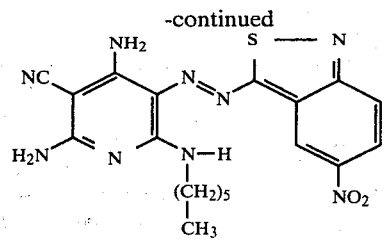

EXAMPLE 37

Dyeing Instructions 1 part of the crude dye obtained according to Example 7 is ground wet with 2 parts of a 50% aqueous solution of the sodium salt of dinaphthylmethanedisulfonic acid and the mixture is dried.

This dye preparation is stirred with 40 parts of a 10% aqueous solution of the sodium salt of oleyl methyltauride and 4 parts of a 40% acetic acid solution are added. By diluting with water, a dyebath of 4,000 parts is prepared from this mixture.

100 parts of a cleaned polyester fibre material are put into this bath at 50°, the temperature is raised to 120° to 130° in the course of half an hour and dyeing is carried out at this temperature for one hour in a closed vessel. The material is then cleaned reductively and rinsed well. A deep yellow dyeing with outstanding fastness to light and sublimation is obtained.

What is claimed is:

1. A compound of the formula

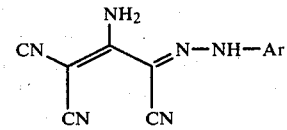

in which Ar is a substituted or unsubstituted phenyl radical or a naphthyl radical wherein the substituents are one or more halogen atoms or nitro, cyano, $C_1$–$C_4$-alkyl, $C_1$–$C_4$-alkoxy, m- or p-carboxyl, aryloxy, $C_1$–$C_4$-alkoxycarbonyl, sulfonamide, carboxamide, acyl, acylamino or phenylazo groups, and the phenyl nucleus in the phenylazo groups can be substituted by chlorine, nitro, cyano, $C_1$–$C_4$-alkyl, $C_1$–$C_4$-alkoxy, $C_1$–$C_4$-alkoxycarbonyl or sulfonamide groups.

2. A compound of the formula

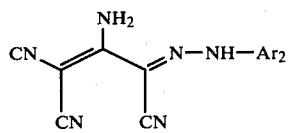

in which $Ar_2$ is a phenyl radical, which can carry one or more halogen atoms or nitro, cyano, $C_1$–$C_4$-alkyl, $C_1$–$C_4$-alkoxy, m- or p-carboxyl, aryloxy, $C_1$–$C_4$-alkoxycarbonyl, sulfonamide, carboxamide, acyl, acylamino or phenylazo groups, and the phenyl nucleus in the phenylazo groups can be substituted by chlorine, nitro, cyano, $C_1$–$C_4$-alkyl, $C_1$–$C_4$-alkoxy, $C_1$–$C_4$-alkoxycarbonyl or sulfonamide groups.

3. A compound of the formula

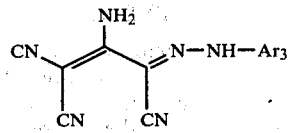

in which $Ar_3$ is a phenyl radical or a 4-nitrophenyl, 2-chloro-4-nitrophenyl, 2-cyano-4-nitrophenyl, 2,4-dinitrophenyl, 2-chloro-4,6-dinitrophenyl or 3- or 4-carboxyphenyl radical.

* * * * *